(12) United States Patent  (10) Patent No.: US 6,682,564 B1
Duarte  (45) Date of Patent: Jan. 27, 2004

(54) INTERVERTEBRAL SUPPORT DEVICE AND RELATED METHODS

(76) Inventor: Luis Duarte, 1512 Darlene St., San Angelo, TX (US) 76904

( * ) Notice: Subject to any disclaimer, the term of this patent is extended or adjusted under 35 U.S.C. 154(b) by 0 days.

(21) Appl. No.: 10/189,309

(22) Filed: Jul. 2, 2002

(51) Int. Cl.[7] .............................. A61F 2/44; A61B 17/56
(52) U.S. Cl. ................................ 623/17.16; 623/17.11; 606/61
(58) Field of Search .......................... 623/16.11, 17.11, 623/17.15, 17.16; 606/61

(56) References Cited

U.S. PATENT DOCUMENTS

| | | | |
|---|---|---|---|
| 5,782,919 A | | 7/1998 | Zdeblick et al. ............... 623/17 |
| 5,865,845 A | * | 2/1999 | Thalgott ................... 623/17.16 |
| 5,888,224 A | * | 3/1999 | Beckers et al. .......... 623/17.16 |
| 5,888,227 A | * | 3/1999 | Cottle ...................... 623/17.16 |
| 5,906,616 A | | 5/1999 | Pavlov et al. .................. 606/61 |
| 5,980,552 A | * | 11/1999 | Pinchasik et al. .......... 623/1.16 |
| 5,984,922 A | | 11/1999 | McKay ......................... 606/61 |
| 5,984,967 A | | 11/1999 | Zdeblick et al. ............... 623/17 |
| 6,039,761 A | * | 3/2000 | Li et al. .................... 623/17.16 |
| 6,045,580 A | | 4/2000 | Scarborough et al. ........ 623/17 |
| 6,059,829 A | * | 5/2000 | Schlapfer et al. ........ 623/17.16 |
| 6,102,950 A | | 8/2000 | Vaccaro ........................ 623/17 |
| 6,117,174 A | | 9/2000 | Nolan ........................ 623/17.11 |
| 6,159,244 A | | 12/2000 | Suddaby ................... 623/17.11 |
| 6,165,219 A | | 12/2000 | Kohrs et al. ............. 623/17.11 |
| 6,193,757 B1 | * | 2/2001 | Foley et al. ............. 623/17.16 |
| 6,200,347 B1 | | 3/2001 | Anderson et al. ........ 623/16.11 |
| 6,277,149 B1 | | 8/2001 | Boyle et al. ............. 623/17.16 |
| 6,302,914 B1 | | 10/2001 | Michelson .................... 623/17 |
| 6,315,795 B1 | | 11/2001 | Scarborough et al. ..... 623/7.11 |
| 6,350,283 B1 | * | 2/2002 | Michelson ............... 623/17.11 |
| 2001/0008980 A1 | | 7/2001 | Gresser et al. ........... 623/17.11 |
| 2001/0031965 A1 | | 10/2001 | Zucherman et al. .......... 606/61 |
| 2001/0034553 A1 | | 10/2001 | Michelson ............... 623/17.11 |
| 2002/0082597 A1 | * | 6/2002 | Fraser ......................... 606/61 |

* cited by examiner

Primary Examiner—Pedro Philogene
Assistant Examiner—David A Bonderer
(74) Attorney, Agent, or Firm—Allen, Dyer, Doppelt, Milbrath & Gilchrist, P.A.

(57) ABSTRACT

An intervertebral support device may include a body having opposing first and second end faces, opposing top and bottom faces extending between the first and second end faces, and opposing side faces extending between the first and second end faces. A first diagonal direction may be defined between a first vertical corner at the first end face and a diagonally opposite second vertical corner at the second end face, and a second diagonal direction defined between a second vertical corner at the first end face and a diagonally opposite first vertical corner at the second end face. The body may have a tapering height decreasing from the first end face to the second end face, and while also tapering more quickly in the first diagonal direction than the second diagonal direction to provide a corrected angle of spinal curvature upon positioning between adjacent vertebral bodies in a human spine.

25 Claims, 4 Drawing Sheets

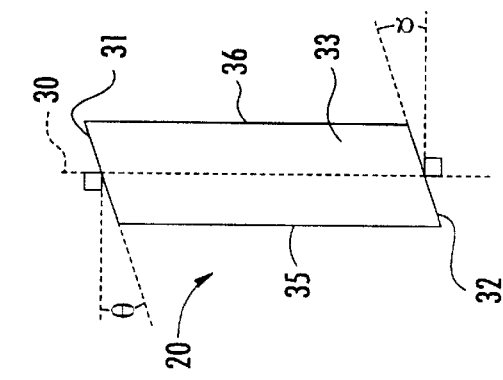
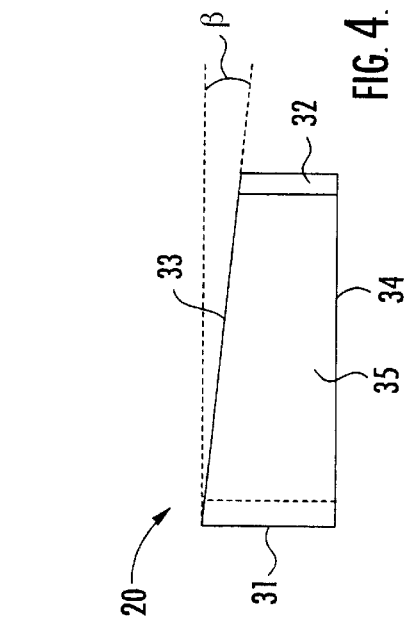
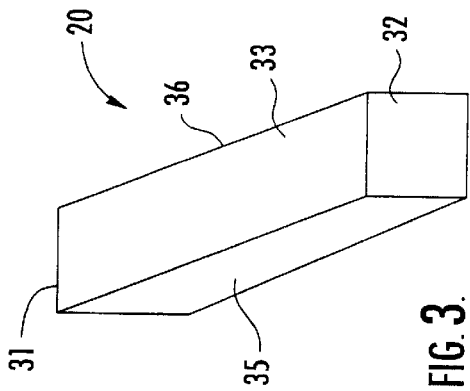
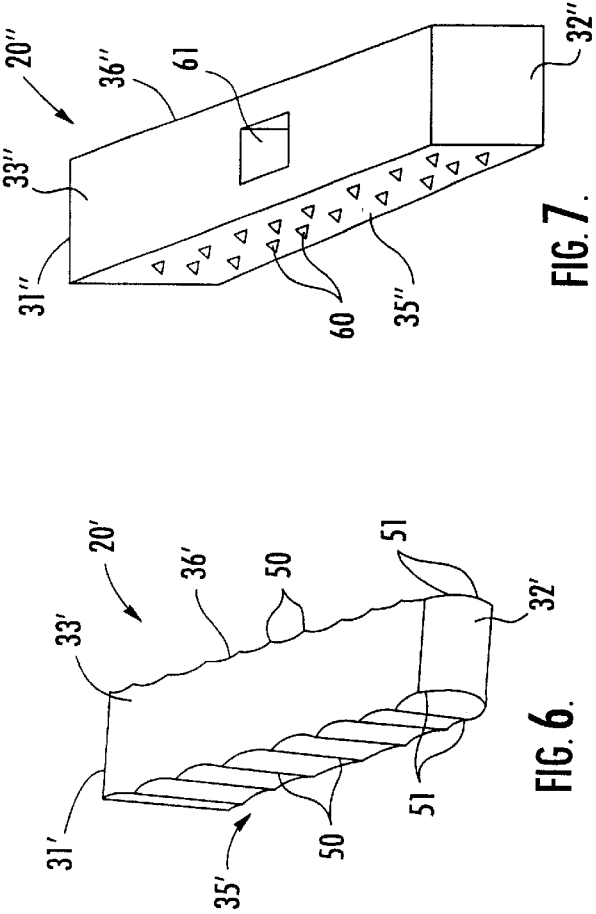

INTERVERTEBRAL SUPPORT DEVICE AND RELATED METHODS

FIELD OF THE INVENTION

The present invention relates to the field of medical devices, and, more particularly, to spinal implants and related methods.

BACKGROUND OF THE INVENTION

A normal human spine has two curves called the kyphotic curve and the lordotic curve. The kyphotic curve is the outward curve of the thoracic vertebrae (at the level of the ribs). The lordotic curve is the inward curve of the lumbar vertebrae (just above the buttocks).

A small degree of both kyphotic and lordotic curvature is normal, but in some circumstances these curves may become exaggerated. Exaggeration of the kyphotic curve is called Scheuermann's disease, and this condition results in rounded or hunched shoulders. Exaggeration of the lordotic curve is called lordosis, or more commonly "swayback." Depending upon the severity of the case, medical (i.e., surgical) intervention is sometimes required to correct the abnormal curvature associated with Scheuermann's disease and lordosis. Similarly, medical intervention is frequently required for a third type of scoliotic or sideways curvature of the spine called scoliosis.

To this end, numerous types of spinal implant devices have been developed to correct or modify an angle of spinal curvature. For example, U.S. Pat. No. 6,277,149 to Boyle et al. discloses a ramp-shaped intervertebral implant formed from the diaphysis or metaphysis of a long bone or other biocompatible material. The implant may also have ridges defined on top and bottom surfaces thereof to help hold the implant in place. Additionally, perforations may be formed along any of the surfaces of the implant to facilitate bone ingrowth.

Another similar implant is disclosed in U.S. Pat. No. 6,302,914 to Michelson, which also has serrations for holding the insert in place as well as holes to allow bone in-growth. Other examples of wedge-shaped or tapered implants are disclosed in U.S. Pat. Nos. 6,045,580 and 6,315,795 both to Scarborough et al.; U.S. Pat. No. 5,984,922 to McKay; and U.S. Pat. No. 6,117,174 to Nolan; and in Published Application Nos. 2001/0031965 to Zucherman et al. and 2001/0008980 to Gresser et al. Each of these implants is designed to be used in pairs, i.e., one is to be inserted on each side of the center of the spine between two vertebral bodies so that both halves of the spine are supported.

While the above devices may be effective for correcting spinal curvature, their insertion may in some instances be quite obtrusive to the patient. That is, to insert two implants between vertebral bodies may require more than one incision by the surgeon as well as movement of several back muscles, ligaments, etc. As a result, significant trauma may be experienced by the patient, which can not only increase his pain but also prolong recovery. Additionally, using multiple spinal implants may be expensive, and they may require a relatively long time for a surgeon to insert in a patient.

SUMMARY OF THE INVENTION

In view of the foregoing background, it is therefore an object of the present invention to provide an intervertebral support device which provides correction for conditions such as lordosis, Scheuermann's disease, and scoliosis, while causing less trauma to a patient during implantation.

This and other objects, features, and advantages in accordance with the present invention are provided by an intervertebral support device for providing a corrected angle of spinal curvature upon positioning between adjacent vertebral bodies of a human spine. The intervertebral support device may include a body having opposing first and second end faces, opposing top and bottom faces extending between the first and second end faces, and opposing side faces extending between the first and second end faces. Furthermore, a first diagonal direction may be defined between a first vertical corner at the first end face and a diagonally opposite second vertical corner at the second end face, and a second diagonal direction defined between a second vertical corner at the first end face and a diagonally opposite first vertical corner at the second end face.

As such, in certain embodiments the body may have a tapering height decreasing from the first end face to the second end face, and while also tapering more quickly in the first diagonal direction than the second diagonal direction. The intervertebral support device thereby provides the corrected angle of spinal curvature upon positioning between adjacent vertebral bodies of the human spine. In other embodiments, the body may alternately (or in addition) have an axis, and the opposing first and second end faces may be canted at respective angles from perpendicular to the axis of the body to thereby provide the corrected angle of spinal curvature upon positioning between adjacent vertebral bodies of the human spine. By way of example, the body may be generally rectangular in shape.

More particularly, the first and second end faces may be canted at greater than about 10° from perpendicular to the axis of the body. Further, the respective angles of canting of the first and second end faces may be substantially equal. Also, the body may further include opposing side faces, and the body may have one or more spikes and/or serrations defined on at least one of the top, bottom, and side faces. The body may further have at least one cavity defined therein for vertebral bone ingrowth.

The tapered height may define a taper angle less than about 10° from the first end face to the second end face, and, more preferably, in a range of about 3–5°. Also, edge portions of at least one of the first and second end faces may be rounded over. In certain embodiments, the body may be hollow, and it may also have a support therein for supporting at least one of the sides. The body may also be a skeletal frame, and it may include at least one of bone, metal, carbon fiber, and PEAK, for example.

A method aspect of the invention is for providing a corrected angle of curvature to a spine in a human patient. The method may include positioning an intervertebral support device, such as the one described briefly above, between adjacent vertebral bodies in the spine and transverse to an imaginary vertical plane bisecting the spine and normal to the posterior thereof to thereby provide the corrected angle of spinal curvature. As such, only a single support device need be used to provide support to both sides of the spine. Thus, less trauma may be required to implant the device as compared to the prior art devices noted above, and the patient may therefore feel less pain following surgery and recover more rapidly.

By way of example, the insertion angle may be greater than about 10°, and more preferably in a range of about 15–30° (and even up to about 90° for certain surgical techniques). The method may also include removing at least some of a spinal disc between the vertebral bodies prior to positioning. Additionally, the support device may be positioned from the posterior or anterior of the spine.

BRIEF DESCRIPTION OF THE DRAWINGS

FIG. 3 is a perspective view of the intervertebral support device of FIG. 1.

FIG. 4 is a side view of the intervertebral support device of FIG. 1.

FIG. 5 is top plan view of the intervertebral support device of FIG. 1 illustrating respective angles of canting of first and second end faces thereof.

FIG. 6 is a perspective view of an alternate embodiment of the intervertebral support device according to the invention.

FIG. 7 is a perspective view of another alternate embodiment of the intervertebral support device according to the invention.

FIG. 8 is a side view of still another alternate embodiment of the intervertebral support device according to the invention.

DETAILED DESCRIPTION OF THE PREFERRED EMBODIMENTS

Figure 2:
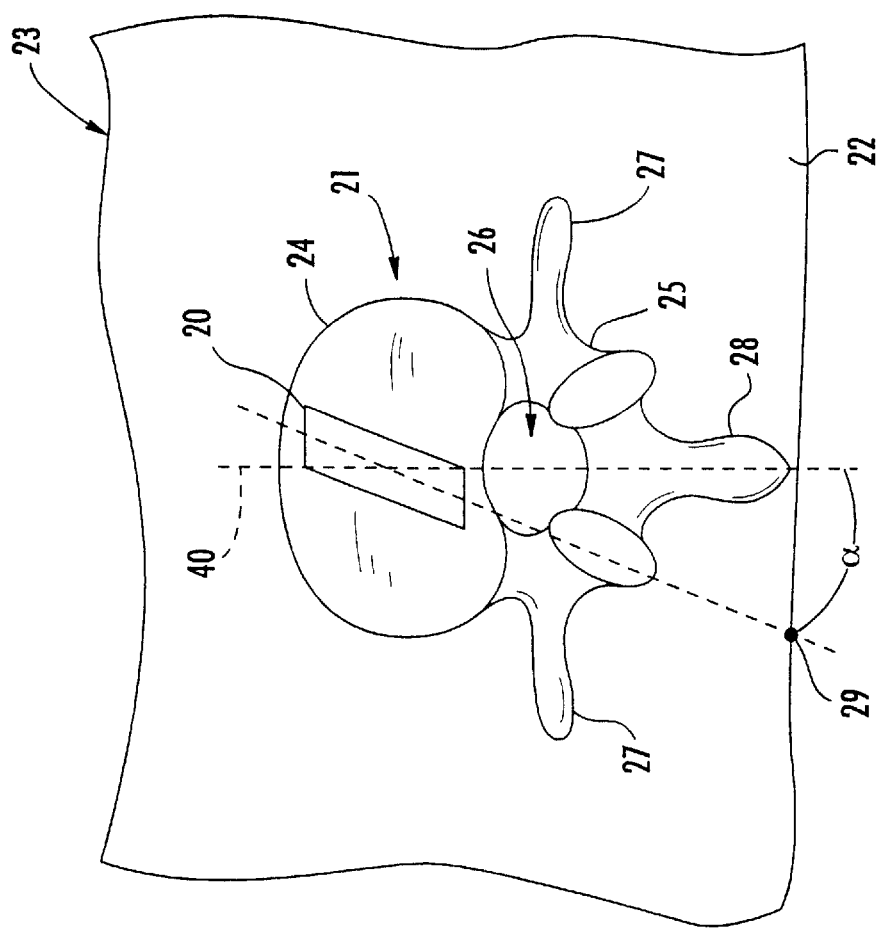
FIG. 2 is a top view of a human vertebra illustrating the insertion of an intervertebral support device in accordance with the invention.
Figure 1:
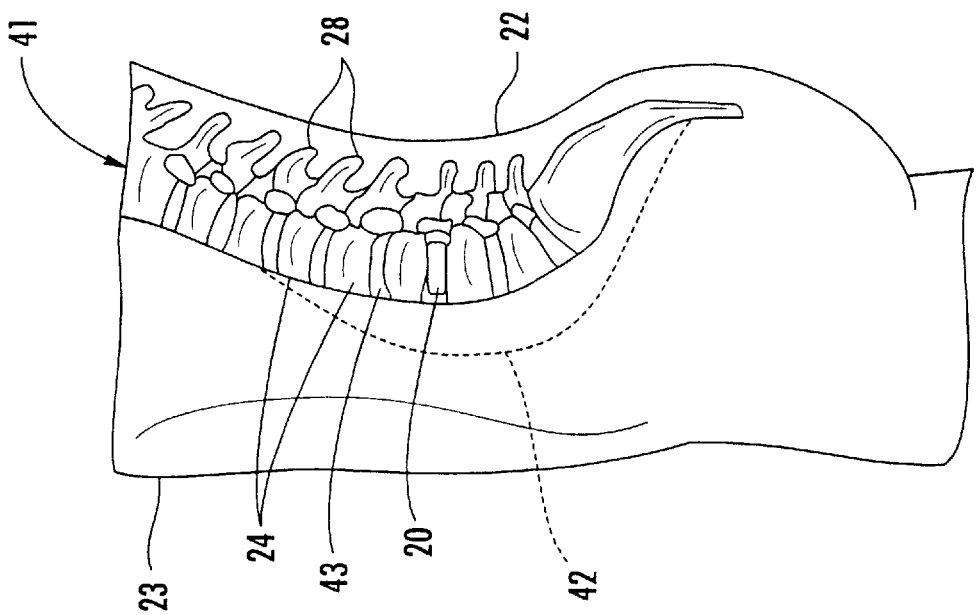
FIG. 1 is a side view of a human spine having an intervertebral support device in accordance with the present invention inserted therein to correct an angle of spinal curvature.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and multiple prime notation are used to indicate similar elements in alternate embodiments.

Referring initially to FIGS. 1–5, an intervertebral support device 20 in accordance with the present invention will now be described. The intervertebral support device 20 is for providing a corrected angle of spinal curvature upon positioning between adjacent vertebrae 21 of a human spine 41 in the back 22 of a patient 23. As used herein, "corrected" angle means any desired modification to an angle of spinal curvature, as will be appreciated by those of skill in the art.

As will also be appreciated by those of skill in the art, each vertebra 21 includes a vertebral body 24, a lamina 25 connected thereto and defining the spinal canal 26 therebetween, and transverse processes 27 and spinal processes 28 connected to the lamina. In accordance with the present invention, the intervertebral support device 20 is particularly well suited for insertion between two adjacent vertebral bodies 24 to provide a corrected angle of spinal curvature, as will be described further below. By way of comparison, an incorrect angle of lordotic curvature is illustratively shown in FIG. 1 with a dashed line 42, which is in contrast to the corrected angle of the spine 41 provided by the intervertebral support device 20.

The intervertebral support device 20 includes a body having an axis 30 and having opposing first and second end faces 31, 32, respectively. The body also includes opposing top and bottom faces 33, 34, respectively, and opposing side faces 35, 36 extending between the first and second end faces 31, 32, to thereby define a generally rectangular shape. Other sides (not shown) may be included in some embodiments to provide different body shapes, such as hexagons, octagons, etc., as will be understood by those of skill in the art.

Moreover, the body illustratively has a tapered height decreasing from the first end face 31 to the second end face 32. This tapered height defines a taper angle β shown in FIG. 4. Furthermore, as may particularly be seen with respect to FIG. 5, the opposing first and second end faces 31, 32 are preferably canted at respective angles θ, γ from perpendicular to the axis 30. The above described tapering (i.e., angle β) and canting of the first and second end faces 31, 32, are selected to provide the corrected angle of spinal curvature upon positioning between adjacent vertebral bodies 24 in the spine 41, as will be described-further below.

The angle β corresponds to the desired angle of correction of spinal curvature required between a given pair of vertebral bodies 24. The taper may vary depending upon the particular spinal condition to be corrected, i.e., lordosis, Scheuermann's disease, scoliosis, etc. That is, the angle β will vary depending upon where the intervertebral support device 20 is to be placed (e.g., between lower lumbar or upper thoracic vertebrae 21) and the amount of correction that is required. The intervertebral support device 20 need not always be used to remedy extreme cases such as scoliosis or Scheuermann's disease, rather slight correction may be provided in some applications to simply maintain normal lordosis and/or sagittal alignment. By way of example, the angle β of the taper will typically be less than about 10° from the first end face 31 to the second end face 32, and in the case of lordosis correction may typically be in a range of about 3–5°, although other angles may also be used.

Of course, the intervertebral support device 20 may include other tapers as well, such as from one of the opposing sides 35, 36 to the other (not shown), for example. Such additional tapers may make the intervertebral support device 20 particularly useful for correcting scoliosis, for example. That is, the taper represented by the angle β may be used to correct the scoliotic curve, while the side-to-side taper may allow the proper kyphotic/lordotic curve to be maintained, as will be appreciated by those of skill in the art. Further, while a linear taper is illustratively shown in FIG. 4, non-linear tapers may also be used in some embodiments.

The first and second end faces 31, 32 are preferably canted such that the canting angles θ, γ are greater than about 10° from perpendicular to the axis 30 of the body. In the embodiment illustrated in FIG. 4, for example, the respective angles of canting θ, γ of the first and second end faces 31, 32 are substantially equal. Of course, in other embodiments these angles may be different.

In one particularly advantageous embodiment, the angles θ, γ may be set such that the first and second end faces 31, 32 are substantially parallel to the back 22 of the patient 23 when inserted at a predetermined insertion angle a illustratively shown in FIG. 2, as will be described further below. This orientation allows the desired height to be maintained adjacent the anterior of the vertebrae 21 as well as adjacent the spinal canal 26 when the intervertebral support device 20 is positioned at the insertion angle α. This would not be possible with the prior art devices described above, since inserting a single one of these devices at such an angle would cause the taller of the two ends thereof to protrude too far inwardly toward the center of the vertebral bodies 24. As a result, the amount of kyphotic/lordotic correction provided may not match the taper of the device, plus this may result in an unwanted scoliotic curve and/or unequal support for both sides of the spine 41.

Dimensions of the intervertebral support device 20 may be defined as follows. Using a length m for the major sides of the bottom face 34, a length n for the major sides of the top face 33, a height of 11 mm for the first end face 31 and a height of 9 mm for the second end face 32, the shape of the top face may be defined according to the following relationship:

$$2x - m \cdot \cos 20° \cdot z = -9m \cdot \cos 20°, \quad (1)$$

where m may be any desired length, and $n = \sqrt{m^{2+4}}$. The height values 9 mm and 11 mm were selected in the above example to provide a 3–5° angle of lordosis, although other values may be used as well for these heights. It will also be noted in the above example that the canting angles θ, γ are both 20°, although here again other angles may also be used.

Numerous alternate embodiments of the invention are illustrated in FIGS. 6–9. Elements not specifically mentioned, but indicated by prime or multiple prime notation, are similar to those described above and need no further discussion herein. The body 20' illustrated in FIG. 6 includes serrations 50 on the opposing sides 35', 36', as well as edge portions 51 of the second end face 32' which are rounded over. Of course, edge portions of the first end face 31' (or other edges of the body) may be rounded over as well, if desired.

In the embodiment illustrated in FIG. 7, the body 20" may include one or more spikes 60. Both the serrations 50 and spikes 60 may be used to help hold the respective intervertebral support devices 20', 20" in place upon positioning between adjacent vertebral bodies 24, as will be appreciated by those of skill in the art. Of course, serrations 50 and/or spikes 60 may be included on any face of the body. The body 20" may further have at least one cavity 61 defined therein for vertebral bone ingrowth to provide an arthrodesis support device. The cavity may extend all the way through the body from the top face 33" to the bottom face 34", or only part way.

In another embodiment the intervertebral support device 20''' may be a skeletal frame, as illustratively shown in FIG. 8. The intervertebral support device 20''' may further include a support 70 for supporting at least one face thereof.

Figure 9:
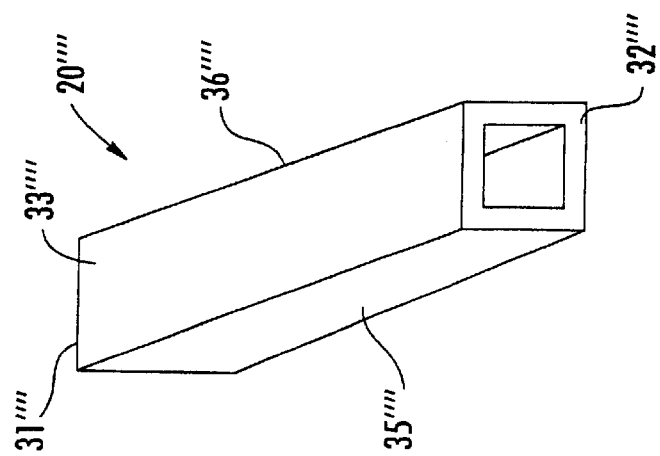
FIG. 9 is a perspective view of yet another alternate embodiment of the intervertebral support device according to the invention.

Yet another embodiment is illustrated in FIG. 9 in which the intervertebral support device 20'''' is hollow. The intervertebral support device 20'''' may also include one or more supports 70 as well in some embodiments. The body may be made of any suitable biocompatible material such as bone, metal (e.g., titanium), carbon fiber, and/or PEAK, for example. Obviously, materials such as bone may be desirable if fusion between the vertebral bodies 24 and intervertebral support device 20 is required.

Figure 10:
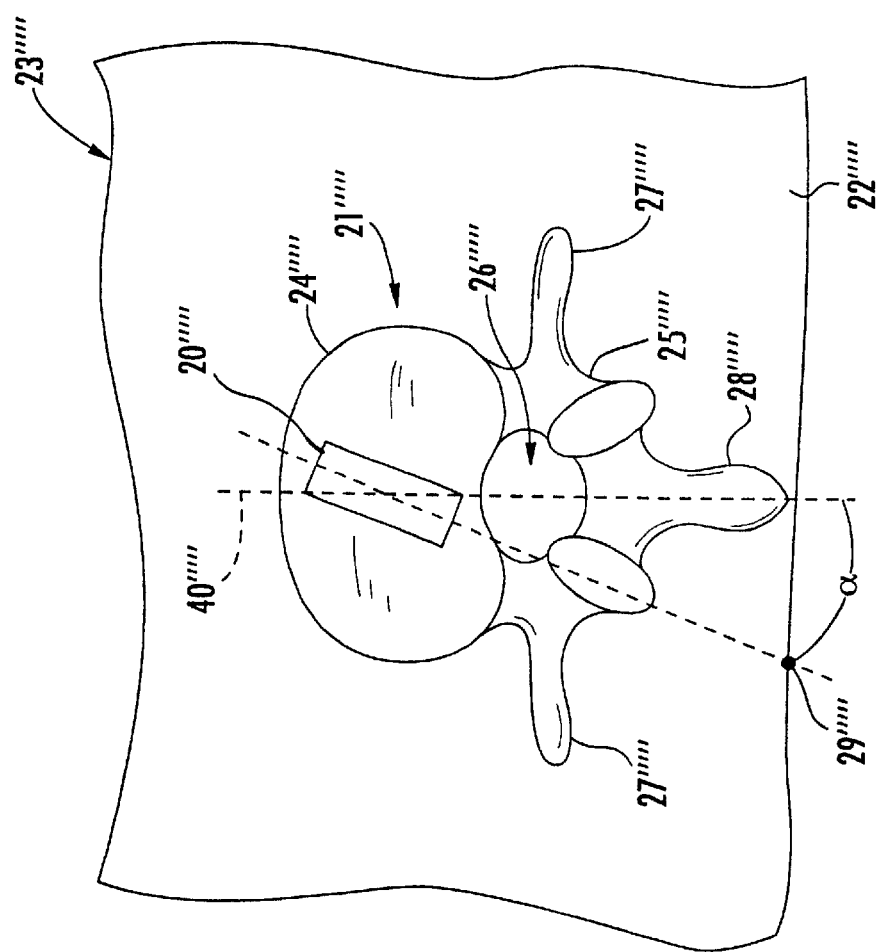
FIG. 10 is a top view similar to FIG. 2 illustrating another alternate embodiment of the intervertebral support device according to the present invention.
Figure 11:
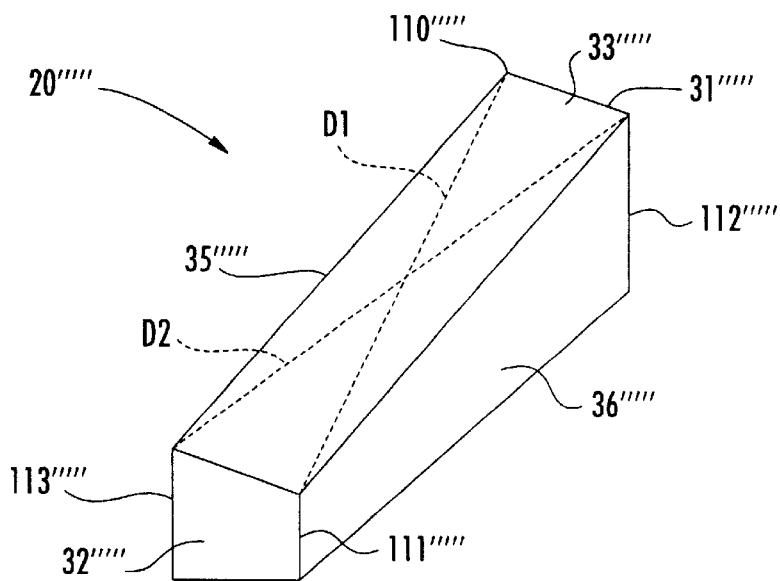
FIG. 11 is a perspective view of the intervertebral support device of FIG. 10.

Turning now additionally to FIGS. 10 and 11, still another embodiment of the intervertebral support device 20''''' will now be described. In the illustrated embodiment, the intervertebral support device 20''''' is similar to that described above with respect FIG. 2 with the exception that the first and second end faces 31''''', 32''''' are not canted. Rather, a first diagonal direction D1 (illustrated with a dashed line) is defined between a first vertical corner 110''''' at the first end face 31''''' and a diagonally opposite second vertical corner 111''''' at the second end face 32'''''. Additionally, a second diagonal direction D2 (also illustrated with a dashed line) is defined between a second vertical corner 112''''' at the first end face 31''''' and a diagonally opposite first vertical corner 113''''' at the second end face 32'''''.

In accordance with the present embodiment, the body not only has a tapering height decreasing from the first end face 31''''' to the second end face 32''''', but it also tapers more quickly in the first diagonal direction D1 than in the second diagonal direction D2 to thereby provide the corrected angle of spinal curvature upon positioning between adjacent vertebral bodies 24''''', as may best be seen in FIG. 11. Of course, those of skill in the art will appreciate that in certain embodiments the intervertebral support device 20''''' may also have canted first and second end faces 31''''', 32''''', as well as one or more of the other features described above (spikes, serrations, rounded end faces, bone ingrowth cavities, etc.). The remaining elements illustrated in FIGS. 6–11 and not specifically mentioned herein are similar to those described above and will therefore not be discussed further.

The intervertebral support device 20 may be manufactured according to a variety of different techniques. For example, with certain of the above materials a mold may be used. Of course, other techniques may include forming a block of the desired material (e.g., a rectangular block) and planning or cutting the block to form the canted first and second end faces 31, 32 and the tapered height therebetween. Other suitable manufacturing techniques known to those of skill in the art may also be used.

Figure 12:
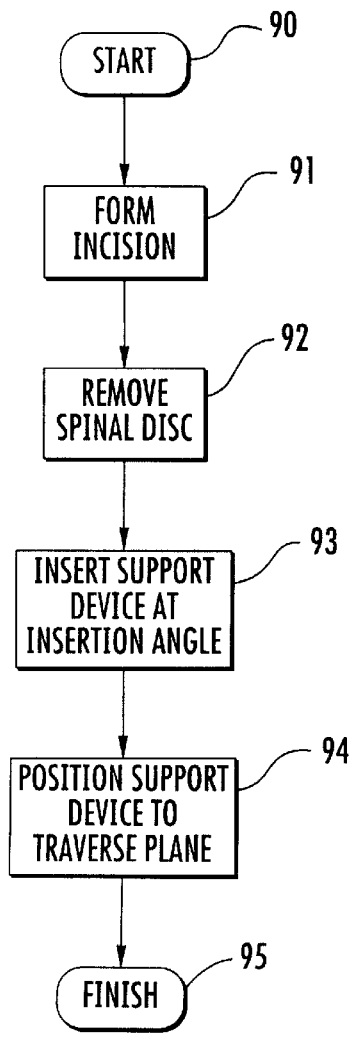
FIG. 12 is a flow diagram illustrating a method for providing a corrected angle of curvature of a spine in a human patient in accordance with the present invention.

A method aspect of the invention for providing a corrected angle of curvature of a spine 41 in a human patient 23 using the above described intervertebral support device 20 will now be described with respect to FIG. 12. The method begins (Block 90) with forming an incision at a point 29 in the patient's back 22 to one side of an imaginary vertical plane 40, which bisects the spine 41 and is normal to the posterior thereof (FIG. 2), at Block 91. Generally, it will be necessary to remove some or all of the spinal disk 43 between the vertebral bodies 24, at Block 92, as well as move certain back muscles/ligaments to allow for insertion of the intervertebral support device 20, as will be appreciated by those of skill in the art.

Thereafter, the intervertebral support device 20 may be inserted though the incision at the insertion angle α, which is measured relative to the imaginary vertical plane 40, at Block 93. In particular, by inserting the intervertebral support device 20 at the insertion angle α, the intervertebral support device may be relatively easily positioned to traverse the imaginary vertical plane 40, at Block 94. As such, only a single support device 20 need be used to provide support to both sides of the spine 41, as will be appreciated by those of skill in the art. Accordingly, less trauma may be required to implant the intervertebral support device 20 as compared to the prior art devices noted above. Thus, the patient may feel less pain following surgery and recover more rapidly.

Of course, more that one intervertebral support device 20 may be used, either between the same two adjacent vertebral bodies 40 or between different pairs of adjacent bodies along the spine 41, as will be appreciated by those of skill in the art. A variety of suitable surgical techniques known to those skilled in the art may be used for performing the steps illustrated at Blocks 91–94, and such steps will therefore not be discussed further herein.

By way of example, the insertion angle α may be greater than about 10°, and more preferably may be in a range of about 15–30°. Insertion angles of up to about 90° (or other angles) may even be used for some surgical techniques. Although a posterior insertion has been described, it should be noted that positioning of the intervertebral support device 20 from the side or anterior of the spine 41 may also be performed, if desired. The method concludes (Block 95) upon closing the incision in the patient's back 22 by any suitable surgical technique, as will be understood by those skilled in the art. It should be noted that although the preceding method has been described as using the intervertebral support device 20 for clarity of explanation, any of the above-described embodiments thereof (or others which will be apparent to those of skill in the art) may also be used.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An intervertebral support device for providing a corrected angle of spinal curvature upon positioning between adjacent vertebral bodies of a human spine, the intervertebral support device comprising:

a body having opposing first and second end faces, opposing top and bottom faces extending between the first and second end faces, and opposing side faces extending between the first and second end faces, a first diagonal direction defined between a first vertical corner at the first end face and a diagonally opposite second vertical corner at the second end face, a second diagonal direction defined between a second vertical corner at the first end face and a diagonally opposite first vertical corner at the second end face;

said body having a tapering height decreasing from the first end face to the second end face, and while also tapering more quickly in the first diagonal direction than the second diagonal direction, to thereby provide the corrected angle of spinal curvature upon positioning between adjacent vertebral bodies of the human spine.

2. The intervertebral support device of claim 1 wherein said body is generally rectangular.

3. The intervertebral support device of claim 1 wherein said body has an axis; and wherein the opposing first and second end faces are canted at respective angles from perpendicular to the axis of said body.

4. The intervertebral support device of claim 3 wherein the first and second end faces are canted at greater than about 10° from perpendicular to the axis of said body.

5. The intervertebral support device of claim 3 wherein the respective angles of canting of the first and second end faces are substantially equal.

6. The intervertebral support device of claim 1 wherein said body has serrations defined on at least one of the top, bottom, and side faces.

7. The intervertebral support device of claim 1 wherein said body has at least one spike on at least one of the top, bottom, and side faces.

8. The intervertebral support device of claim 1 wherein said body has at least one cavity defined therein for vertebral bone ingrowth.

9. The intervertebral support device of claim 1 wherein the tapered height defines a taper angle less than about 10° from the first end face to the second end face.

10. The intervertebral support device of claim 9 wherein the tapered height defines a taper angle in a range of about 3–5° from the first end face to the second end face.

11. The intervertebral support device of claim 1 wherein edge portions of at least one of the first and second end faces are rounded over.

12. The intervertebral support device of claim 1 wherein said body is hollow.

13. The intervertebral support device of claim 1 further comprising a support within said body for supporting at least one of the faces.

14. The intervertebral support device of claim 1 wherein said body comprises a skeletal frame.

15. The intervertebral support device of claim 1 wherein said body comprises at least one of bone, metal, carbon fiber, and PEAK.

16. An intervertebral support device for providing a corrected angle of spinal curvature upon positioning between adjacent vertebral bodies of a human spine, the intervertebral support device comprising:

a body having an axis, opposing first and second end faces, and opposing top and bottom faces extending between the first and second end faces;

said body having a tapered height decreasing from the first end face to the second end face, and the opposing first and second end faces being canted at respective angles from perpendicular to the axis of said body to thereby provide the corrected angle of spinal curvature upon positioning between adjacent vertebral bodies of the human spine.

17. The intervertebral support device of claim 16 wherein said body is generally rectangular.

18. The intervertebral support device of claim 16 wherein the first and second end faces are canted at greater than about 10° from perpendicular to the axis of said body.

19. The intervertebral support device of claim 16 wherein the respective angles of canting of the first and second end faces are substantially equal.

20. The intervertebral support device of claim 16 wherein said body has serrations defined on at least one of the top, bottom, and side faces.

21. The intervertebral support device of claim 16 wherein said body has at least one spike on at least one of the top, bottom, and side faces.

22. The intervertebral support device of claim 16 wherein said body has at least one cavity defined therein for vertebral bone ingrowth.

23. The intervertebral support device of claim 16 wherein the tapered height defines a taper angle less than about 10° from the first end face to the second end face.

24. The intervertebral support device of claim 23 wherein the tapered height defines a taper angle in a range of about 3–5° from the first end face to the second end face.

25. The intervertebral support device of claim 16 wherein edge portions of at least one of the first and second end faces are rounded over.

* * * * *